(12) United States Patent
Bernaert et al.

(10) Patent No.: US 8,765,191 B2
(45) Date of Patent: Jul. 1, 2014

(54) COCOA EXTRACTS FOR USE IN PROVIDING SKIN BENEFITS

(75) Inventors: Herwig Bernaert, Lebbeke-Wieze (BE); Leen Allegaert, Lebbeke-Wieze (BE)

(73) Assignee: Barry Callebaut AG, Zurich (CH)

( * ) Notice: Subject to any disclaimer, the term of this patent is extended or adjusted under 35 U.S.C. 154(b) by 0 days.

(21) Appl. No.: 12/682,081

(22) PCT Filed: Sep. 26, 2008

(86) PCT No.: PCT/EP2008/008279
§ 371 (c)(1),
(2), (4) Date: Aug. 6, 2010

(87) PCT Pub. No.: WO2009/046901
PCT Pub. Date: Apr. 16, 2009

(65) Prior Publication Data
US 2010/0297274 A1   Nov. 25, 2010

(30) Foreign Application Priority Data

Oct. 8, 2007  (GB) .................................. 0719543.1

(51) Int. Cl.
*A61K 36/00*   (2006.01)

(52) U.S. Cl.
USPC ....................................................... 424/725

(58) Field of Classification Search
None
See application file for complete search history.

(56) References Cited

U.S. PATENT DOCUMENTS

| | | | |
|---|---|---|---|
| 5,338,554 A | 8/1994 | Vogt et al. | |
| 6,927,280 B2 | 8/2005 | Kochhar et al. | |
| 7,115,285 B2 | 10/2006 | McKee et al. | |
| 7,122,574 B2 | 10/2006 | Romanczyk, Jr. et al. | |
| 2002/0064584 A1 | 5/2002 | Kealey et al. | |
| 2003/0170199 A1 | 9/2003 | Leclere | |
| 2004/0005347 A1 | 1/2004 | Ter Laak et al. | |
| 2004/0096566 A1* | 5/2004 | Lecoupeau et al. | 426/593 |
| 2006/0134179 A1 | 6/2006 | Takagaki et al. | |
| 2006/0210653 A1 | 9/2006 | Gardiner et al. | |
| 2007/0148107 A1 | 6/2007 | Sies et al. | |

FOREIGN PATENT DOCUMENTS

| | | |
|---|---|---|
| CN | 1089095 | 7/1994 |
| CN | 1397201 | 2/2003 |
| EP | 1787970 | 5/2007 |
| EP | 1541127 | 12/2008 |
| FR | 2734478 | 11/1996 |
| FR | 2885050 | 4/2005 |
| WO | WO 96/10404 | 4/1996 |
| WO | WO 98/09533 | 3/1998 |
| WO | WO 99/45788 | 9/1999 |
| WO | WO 03/079998 | 10/2003 |
| WO | WO 2006/000992 | 1/2006 |
| WO | WO 2006/117465 | 11/2006 |
| WO | WO 2006/117466 | 11/2006 |
| WO | WO 2007/002883 | 1/2007 |
| WO | WO 2007/042745 | 4/2007 |
| WO | WO 2007/082703 | 7/2007 |
| WO | WO 2008/131910 | 11/2008 |
| WO | WO 2008/131911 | 11/2008 |
| WO | WO 2008/131912 | 11/2008 |
| WO | WO 2009/092606 | 7/2009 |
| WO | WO 2009/127407 | 10/2009 |

OTHER PUBLICATIONS

An et al., Physiological activity of irradiated green tea polyphenol on the human skin, am. J. Chin. Med. 33(4):535-46 (2005), Pubmed Abstract, PMID: 16173528.

Chiu et al., Double-Blinded, Placebo-controlled trial of green tea extracts in the clinical and histologic appearance of photoaging skin, Dermatol Surg; 31(7 pt 2):855-60—Pubmed Abstract, PMID 16029678 (Jul. 2005).

Heinrich et al., Long-Term Ingestion of High Flavanol Cocoa Provide Photoprotection against UV-induced Erythema and Improves Skin Condition in Women, J. or Nutrition; 136:1565-69 (Jun. 1, 2006).

Singleton, V.L., et al., Analysis of Total Phenols and Other Oxidation Substrates and Antioxidants by Means of Folin-Ciocalteu Reagent, Methods in Enzymology, 1999, pp. 152-178, vol. 299. (Abstract).

Williams et al., Eating Chocolate Can Significantly Protect the Skin from UV Light, J. of Cosmetic Dermatology; 8:169-173 (2009).

www.cirkuhealth.com/Cocoa-101/CocoaPro.aspx, last accessed Jun. 28, 2010.

www.goodskinsite.com, last accessed Jun. 28, 2010.

www.marsbotanical.com, last accessed Jun. 28, 2010.

\* cited by examiner

*Primary Examiner* — Terry A McKelvey
*Assistant Examiner* — Randall Winston
(74) *Attorney, Agent, or Firm* — Hoxie & Associates LLC

(57) ABSTRACT

A cocoa extract obtainable by the extraction of non-defatted cocoa beans which have not been fermented or have been allowed to ferment for no more than three days, having a polyphenol content of more than 25% by weight, may be used to provide skin benefits by oral administration.

18 Claims, No Drawings

COCOA EXTRACTS FOR USE IN PROVIDING SKIN BENEFITS

CROSS REFERENCE TO RELATED APPLICATIONS

This application is a United States Application under 35 U.S.C. 371 claiming benefit of PCT Application No. PCT/EP2008/008279, filed on Sep. 26, 2008, which claims the benefit of Great Britain Application No. 0719543.1, filed on Oct. 8, 2007 the contents of each of which are incorporated herein by reference.

This invention relates to a cocoa extract and to its uses. In particular, the invention relates to uses of cocoa extracts for skin benefits.

Chocolate and cocoa are popularly claimed to have a plethora of positive effects, including stimulant, relaxant, euphoriant, aphrodisiac, tonic and antidepressant properties. However, the scientific basis for these claims has been elusive. Certainly, depression may in some individuals lead to a craving for sweet foods, and people may receive a transitory uplift in mood from the pleasure of consuming chocolate or from relief of hypoglycemia due to consumption of the sugar in the chocolate. However, the various chemicals in chocolate (other than sugar) suggested to have potentially psychoactive or mood altering effects are generally not present at pharmacologically effective levels.

Cocoa for the production of chocolate is made from the dried and partially fermented seeds of the cacao tree. The harvested cacao pods are opened, the pulp and cocoa beans are removed, and the rind is discarded. The pulp and beans are then piled in heaps, placed in bins, or laid out on grates for usually 6-7 days, during which time the thick pulp liquifies as it ferments. The fermented pulp trickles away, leaving the cocoa beans behind to be collected, dried and further processed to make cocoa butter and cocoa powder. In some instances, the product is treated with alkali to reduce the acidity of the powder. Fermentation is important for the quality and flavor of the beans, which originally have a strong bitter taste. Unfermented or underfermented cocoa beans have a flavor similar to raw potatoes, are very susceptible to mildew and fungal growth, and therefore are not used in the manufacture of chocolate for food consumption. The cocoa bean without its shell is known as a "cocoa nib".

Cocoa is known to contain polyphenols and other biologically active compounds such as xanthines, including theobromine and caffeine.

Cocoa extracts containing polyphenols have been proposed for a number of uses. For example, WO 96/010404 describes cocoa extracts containing proanthocyanidins that are said to be anti-neoplastic. U.S. Pat. No. 7,122,574 discloses polyphenol-containing cocoa extracts that can be used for treating hypertension. WO 03/079998 states that cocoa extracts containing polyphenols can be used in the treatment of diseases involving defective gap junctional communication.

Actives in cocoa extracts other than polyphenols have also been used in an attempt to achieve physiological effects. For example, U.S. Pat. No. 6,927,280 discloses a cocoa albumin and its uses. U.S. Pat. No. 7,115,285 relates to a composition, comprising theobromine or a salt thereof, for suppressing appetite and cravings for substances such as nicotine, coffee, sweets or chocolate while improving energy and enhancing mood. WO 2007/042745 discloses a composition comprising chocolate which is enhanced with theobromine and reviews the active components in chocolate, stating that cocoa contains a number of chemical substances whose influence on human and/or animal physiology is not fully understood, including phenylethylamine and tyramine which act as neurotransmitters and may effect mood swing by causing an emotional high, which can be associated with a feeling of alertness and contentment.

US 2007/0148107 describes a method of reducing UV-induced skin erythema and/or photoaging in a subject in need thereof comprising orally administering to the subject a composition comprising an effective amount of a cocoa component.

FR 2885050 A1 discloses a slimming cosmetic and/or pharmaceutical composition for the treatment of the adipocytes of skin which comprises a cocoa extract containing polyphenols. There is no mention of exactly how the cocoa extract is obtained.

US 2006/0134179 relates to a health food product comprising proanthocyanidins, ascorbic acid or a derivative thereof, and L-cysteine or a derivative thereof. The product is said to provide an excellent beautification (skin-beautifying) effect.

WO 02/14251 (and US 2004/0096566) describes a method for obtaining cocoa bean polyphenol extracts by solvent extraction of fresh cocoa beans. The extracts have cosmetic, food and therapeutic uses and may contain increased levels of beta-sito sterol.

WO 2007/082703 relates to the use of cocoa polyphenols, which may be produced by the method described in WO 02/14251, in beer production.

US 2003/0170199 describes cosmetic and/or dermatological compositions based on cocoa extracts.

WO 2006/117465 and WO 2006/117466 relate to cocoa polyphenols for topical application to the skin in order to control skin pigmentation or for cell cycle regulation.

WO 98/09533 describes cocoa components having an enhanced polyphenol content and their medical uses.

There remains a need for orally administrable compositions that are useful for providing skin benefits, particularly compositions that are derived from natural products. There also remains a need for compositions having these benefits that can be readily incorporated into formulations for oral consumption. For example, the compositions for incorporation into foods and beverages are desirably readily dispersible and impart a good appearance to the product, in terms of colour and/or texture.

According to the invention, there is provided a cocoa extract obtainable by the extraction of non-defatted cocoa beans which have not been fermented or have been allowed to ferment for no more than three days, having a polyphenol content of more than 25% by weight, for use in providing skin benefits by oral administration.

In another aspect, the invention provides the use of a cocoa extract obtainable by the extraction of non-defatted cocoa beans which have not been fermented or have been allowed to ferment for no more than three days, having a polyphenol content of more than 25% by weight, in the manufacture of a medicament for use in providing skin benefits by oral administration.

In a further aspect, the invention provides a method for providing skin benefits in a subject, comprising orally administering to said subject an effective amount of a cocoa extract obtainable by the extraction of non-defatted cocoa beans which have not been fermented or have been allowed to ferment no more than three days, having a polyphenol content of more than 25% by weight.

It has been found that the extracts according to the invention, prepared from non-defatted cocoa beans which have not been fermented or have been fermented for a short time, such as less than three days, have advantages in terms of their effect on skin after oral consumption. This was surprising. Most of the known cocoa extracts that are asserted as having physiological effects are derived from defatted and/or fermented beans, which are often also roasted. The effect, which is systemic rather than topical, is very different from that achieved by the topical application of cocoa extracts.

The extract of the invention is typically a brown-coloured, free-flowing powder. Usually, the extract will have no noticeable odour.

The extract of the invention preferably has a polyphenol content of at least 27% by weight, more preferably at least 30% by weight, even more preferably at least 40% by weight, such as at least 45% by weight. The upper limit for the polyphenol content is typically about 70% by weight. Thus, preferred amounts of polyphenol include from 30% to 70%, from 35% to 70%, from 40% to 70%, from 45% to 65% and from 45% to 60%, the percentages being by weight of the extract. The percentages of polyphenols are preferably expressed as gallic acid equivalents, according to the Folin-Ciocalteu method (e.g., as described in Singleton V L, Orthofer R, Lamuela-Raventos R M. Analysis of total phenols and other oxidation substrates and antioxidants by means of Folin-Ciocalteu reagent. Meth Enzymol 1999; 99: 152-178).

Polyphenols in the extracts of the invention typically comprise monomers and oligomers. Preferably, the extracts of the invention comprise up to 10% by weight of each of monomers, dimers, trimers, tetramers, pentamers, hexamers, heptamers, octamers, nonamers and decamers, and higher oligomers in an amount of up to 15% by weight. More preferably, extracts of the invention comprise, by weight of the extract, 5-10% monomers (preferably including at least 5% epicatechin), 5-10% dimers, 5-10% trimers, 2-8% tetramers, 2-8% pentamers, 2-8% hexamers, 0.5-5% heptamers, 0.1-4% octamers, 0.1-3% nonamers and 0.05-2% decamers, and 5-12% higher oligomers.

Extracts of the invention may contain xanthines (preferably methylxanthines), such as caffeine and theobromine. Caffeine may be present together with theobromine, typically at a weight ratio of theobromine to caffeine in the range of from 20:1 to 5:1. In one embodiment of the invention, the theobromine content is at least 5% by weight, and preferably from 5 to 11% by weight. In this embodiment, the composition preferably has a weight ratio of from 7:1 to 12:1 polyphenol:theobromine. In an alternative embodiment, the extract may be treated, for example with supercritical carbon dioxide, to lower the theobromine content and the content of other xanthines that may be present. A method for lowering the content of theobromine in extracts of this type is described in Example 2.3 of WO 2007/082703, the contents of which are incorporated herein by reference. In this alternative embodiment, the extract has a theobromine content of less than 5% by weight, such as less than 4.5% by weight, for example from 0.1 to 4% by weight.

The extracts of the invention are prepared from cocoa beans that are non-defatted and have not been fermented or have been allowed to ferment for no more than three days. The cocoa beans will typically not have been roasted. Thus, the cocoa beans that are used as the starting material for the production of the extracts of the invention are very different from the cocoa beans that are used to produce cocoa powder and chocolate. Typically, the extracts are prepared from cocoa nibs which are deshelled cocoa beans that are unfermented and non-roasted.

The cocoa beans are preferably obtained by a process that comprises: harvesting and hulling cocoa beans; preventing fermentation of the beans or allowing the beans to ferment for no more than three days (more preferably less than two days, even more preferably less than one day) before halting the fermentation process by drying.

The fat content of the non-defatted cocoa beans, or of the cocoa nibs, that are used in the invention, is typically greater than 30% by weight, more preferably greater than 35% by weight, even more preferably greater than 40% by weight, such as greater than 45% by weight; for example, greater than 50% by weight.

Extracts of the invention are preferably obtainable by solvent extraction of the cocoa beans. The solvent is preferably selected from C1 to C6 alcohols or C1 to C6 ketones, and mixtures thereof, optionally in admixture with water, such as, for example, ethanol, acetone, 2-butanol, 2-propanol and mixtures thereof, optionally in admixture with water. A particularly preferred solvent comprises a mixture of water and acetone in a weight ratio of water:acetone of from 1:1 to 1:9. Preferably, solvent extraction is carried out using a counter current process for a time and at a temperature to achieve the desired degree of extraction, typically from one hour to 2 days at from 20 to 60° C. After extraction, the liquid solvent extract is evaporated to remove a part of the solvent and then spray dried. To improve its solubility, the extract powder is preferably agglomerated in a fluidised bed. The xanthine (and theobromine) content of the extract may be reduced by extraction with super-critical carbon dioxide after the solvent has been removed.

Processes that may be used for producing the extracts of the invention are described in WO 2007/082703 and WO 02/14251, the contents of which are incorporated herein by reference.

Extracts of the invention preferably comprise less than 2% by weight phenylethylamine.

Extracts of the invention may comprise other components derived from the cocoa beans such as protein and sugars. Typically, the extracts comprise from 15 to 40% by weight protein, such as from 20 to 30% by weight protein. The extracts may comprise from 2 to 12% by weight sugars, such as from 4 to 10% by weight sugars.

The extracts of the invention comprise cocoa fats. The term "fats" as used in this context includes lipid material in cocoa beans such as sterols, lipids and phospholipids, as well as mono-glycerides and di-glycerides. Without wishing to be bound by theory, it is believed that these one or more components of the cocoa fats contribute to the beneficial physiological effects of the extracts of the invention. Preparing the extracts of the invention from cocoa beans which have not been defatted or fermented for any substantial length of time increases the amounts of these fat components compared to extracts from defatted beans or beans that have been fermented.

Preferably, the extracts of the invention comprise from 0.1 to 10% by weight of cocoa fats, such as from 0.2 to 8%, or from 0.3 to 7%, or from 0.5 to 5%, or from 0.7 to 3%, by weight of cocoa fats. Preferably, the cocoa fats are non-triglyceride lipids.

An example of a preferred extract of the invention comprises:

(i) from 35 to 70% by weight cocoa polyphenols;
(ii) from 1 to 10% by weight xanthines;
(iii) less than 2% by weight phenylethylamine; and
(iv) from 0.1 to 10% by weight of cocoa fats.

Another extract of the invention comprises by weight 50-60% polyphenols, 7-10% theobromine, and less than 2% phenylethylamine. For example, this extract may comprise by weight 54-58% polyphenols, 8-9% theobromine, and 0.5-

1.5% phenylethylamine. In these compositions, the fat content is preferably no more than 1% and/or the sugar content is no more than 3%.

One or more extracts of the invention may be admixed to form a mixed extract composition.

The extracts are used in the invention for providing skin benefits (preferably in a human). The term "skin benefits" is used herein to refer to one or more desirable effects in skin, including general improvements in skin health. Skin benefits include, for example, one or more of: increased firmness, increased elasticity, increased tonicity, reduced wrinkles (including wrinkle width and/or volume), reduced fine lines, increased hydration, decreased skin roughness, decreased scaling, improved skin structure (including skin barrier). Another skin benefit is depigmenting (or lightening) age spots. Preferably, the skin benefit does not comprise reducing UV-induced skin erythema and/or photoaging. The skin benefits are preferably obtained on the skin of the face, the skin of the body or both.

Preferably, extracts and compositions of the invention do not comprise ascorbic acid or a derivative thereof (such as a salt or a glycoside of ascorbic acid) and/or L-cysteine or a derivative thereof (such as a dimer or N-acetyl cysteine).

The extracts of the invention are formulated for oral consumption and are not intended for topical application. The extracts are consumed in a form that is edible and non-toxic. For example, the extract may be provided as part of a foodstuff or confectionery product. Typically, the extract will be included in the foodstuff or confectionery product in an amount of from 0.1% to 50% by weight, such as from 0.5% to 10% by weight.

Foodstuffs and confectionery products include, for example, those having a fat continuous phase as well as those having a water continuous phase. Foodstuffs include foods and beverages.

Beverages include those adapted for consumption hot or cold. Beverages include one or more additives selected from sweeteners, flavouring agents, colouring agents, stabilisers and preservatives. Beverages will typically comprise from 50% to 99% water. Beverages will typically comprise the extracts of the invention dispersed and/or suspended therein. The extract of the invention is preferably incorporated into the beverage in an amount of from 0.1 to 10% by weight. The extract of the invention may be formulated as a powder which can be converted to a beverage on the addition of water and mixing.

A particularly preferred beverage is a cocoa-flavoured drink. Cocoa-flavoured drinks may comprise: cocoa powder (such as full fat or reduced fat cocoa powder); and optionally milk or a product derived from milk (such as skimmed milk powder) and/or a sweetener. Sweeteners include sugars and non-saccharide sweeteners. Cocoa-flavoured drinks may be formulated to be consumed hot (such as hot chocolate) or cold (such as milk shake).

Foodstuffs typically comprise one or more of protein, fat and carbohydrate. Foodstuffs include dairy products and confectionery products. A preferred foodstuff comprises vegetable fat and/or cocoa butter. Particularly preferred foodstuffs include chocolate and chocolate-like products comprising cocoa solids and sugar. For example, the extracts of the invention may be included in conventional chocolate or chocolate-like products in amounts of from 0.1% to 50% by weight, such as from 0.5% to 25% by weight.

Chocolate or chocolate-like products preferably comprise one or more components selected from the group consisting of cocoa materials, sugars, sugar substitutes, milk powders, fat, emulsifier, flavouring agents and mixtures thereof. Preferably, the cocoa materials are selected from cocoa powder, cocoa mass, cocoa liquor, cocoa butter and mixtures thereof. Milk powders include, for example, skimmed milk powder, whey powder and derivatives thereof, full cream milk powder and mixtures thereof. Suitable sugars include sucrose, fructose, glucose and dextrose and mixtures thereof (with sucrose being preferred). Sugar substitutes preferably include inulin, dextrin, isomaltulose, polydextrose and maltitol and mixtures thereof. Fats include butter fat or fractions thereof, palm oil or fractions thereof, coconut or fractions thereof, palm kernel oil or fractions thereof, liquid oils (for example, sunflower oil and/or rapeseed oil), interesterified mixtures of the above fats or fractions or hardened components thereof, or mixtures thereof. Emulsifiers include lecithin, fractionated lecithin and PGPR or mixtures thereof. Flavouring agents include vanilla and caramel or mixtures thereof.

Chocolate and chocolate-like products may comprise one or more food additives such as biscuit, nuts (whole or pieces), crispies, sponge, wafer or fruit, such as cherries, ginger and raisins or other dried fruit. These additives are normally embedded in the product.

Alternatively, the extract may be provided as a cosmetic composition or supplement.

Cosmetic compositions are preferably in the form of tablets, pills, capsules, caplets, multiparticulates including: granules, beads, pellets and micro-encapsulated particles; powders, elixirs, syrups, suspensions and solutions. Cosmetic compositions will comprise an acceptable diluent or carrier. Orally administrable compositions may be in solid or liquid form and may take the form of tablets, powders, suspensions and syrups. Optionally, the compositions comprise one or more flavouring and/or colouring agents. Carriers suitable for use in such compositions are well known in the art. The compositions of the invention may contain 0.1-99% by weight of the extract.

Supplements may, for example, comprise the extract in liquid form (e.g., as a solution, dispersion or suspension) and/or encapsulated in a capsule. Supplements (which term includes dietary and nutritional products) may take the form of a soft gel or a hard capsule comprising an encapsulating material, preferably selected from the group consisting of gelatin, glycerol, starch, modified starch, starch derivatives such as glucose, sucrose, lactose and fructose. The encapsulating material may optionally contain cross-linking or polymerizing agents, stabilizers, antioxidants, light absorbing agents for protecting light-sensitive fills, preservatives and the like. Preferably, the amount of the extract in the food supplements is from 1 mg to 1000 mg (such as from 50 to 500 mg).

As used herein, the term "effective amount" refers to the amount of an extract or composition which is effective, upon single or multiple dose administration to a subject for achieving one or more skin benefits. An effective amount of the extracts of the invention, is in general, about 0.1 to 20 g/day, e.g., 1-10 g/day for an adult human, most preferably from 0.5 to 5 g/day. The daily dose may be administered once per day, or in divided doses.

The term "administering" and related terms used herein includes consumption of an extract or composition or other product and does not necessarily imply the involvement of any medically qualified personnel. The extracts, compositions and other products can, for example, be administered by the subject simply consuming the extract, composition or other product, such as a food or beverage, after having purchased it his- or herself, independently of any supervision or treatment regimen.

The listing or discussion of an apparently prior-published document in this specification should not necessarily be taken as an acknowledgement that the document is part of the state of the art or is common general knowledge.

The following non-limiting examples illustrate the invention and do not limit its scope in any way. In the examples and throughout this specification, all percentages, parts and ratios are by weight unless indicated otherwise.

EXAMPLE 1

Extract

An extract was prepared by extraction of cocoa nibs (deshelled cocoa beans unfermented and non-roasted) in a counter-current process with the use of a 70/30 mixture of acetone/water. The liquid extract is evaporated and then spray-dried. To improve solubility, the extract powder is agglomerated in a fluidised bed.

The extract had the following composition (% by weight):
Polyphenols 47.5
Ash 4.3
Xanthines 6.9
Moisture 3.5
Fat 1.5
Sugars 6.1
Proteins 24.5
Fibres 5.5
Others 0.2

The polyphenol content (as % by weight of total polyphenols) was as follows:
Monomers 8.2 (7.15% epicatechin and 1.04% catechin)
Dimers 7.1
Trimers 7.3
Tetramers 4.4
Pentamers 3.8
Hexamers 3.5
Heptamers 1.4
Octamers 0.9
Nonamers 1.1
Decamers 0.4
Higher 9.5

No gallic acid or gallic acid derivatives were detected.

The bio-efficiency of a polyphenol rich cocoa extract according to the invention on skin health can be evaluated. Skin hydration, anti-wrinkle and skin structure are typically analysed.

The results are typically determined by biometrics, using a questionnaire and measuring the anti-wrinkle effect.

Evaluation of the anti-wrinkle effect is typically carried out by taking a silicone imprint on day 0 and after 50-100 days of exact zones (crowsfeet, forehead) and then employing 3-dimensional reconstruction with a technique based on a fringes projection system. The 3D surface is described based on calculated parameters x, y z (special pc software (Optocat)) for depth ($\mu$m), width (mm) and volume ($mm^3$).

EXAMPLE 2

The effect of cocoa extracts on skin health (hydration, skin structure, skin barrier function) was evaluated.
Protocol 45 men or women (average age 42 years) were randomized to consume daily during 28 days one of the following three compositions:
 Control: placebo capsules containing micro-crystalline cellulose and no flavanols;
 Invention: cocoa extract from non-defatted beans, containing 300 mg flavanols; and
 Comparative Example: cocoa extract from defatted cocoa beans, containing 300 mg flavanols.

The cocoa polyphenolic extract composition of the invention was prepared from non-defatted cocoa beans generally as described in Example 1 but having a comparable polyphenol content to the extract of the Comparative Example described below.

The composition for the Comparative Example was prepared as follows.

Defatted cocoa cakes were ground in a homogenizer (Waring blender) and a portion of hexane was added. The mixture was stirred for 30 minutes at room temperature and at about 400 rpm. After 30 minutes, this mixture was filtered through a glass filter type 3. The residue was recovered and dried under high vacuum using an oil pump. This residue was extracted with another amount of hexane using the same extraction conditions. The residue was recovered and dried under high vacuum for further extraction using acetone/water. The cocoa powder, that was obtained on the filter after two hexane extractions and dried under high vacuum, was extracted using a mixture of acetone/water (1/1, v/v) with 0.5% acetic acid added (pH=3). This mixture was stirred for 30 minutes at room temperature and at about 400 rpm. After 30 minutes, this mixture was filtered through a glass filter type 3. The residue was recovered and extracted with an additional amount of a mixture of acetone/water (1/1, v/v) with 0.5% acetic acid added (pH=3) using the same extraction conditions. The filtrates were combined and the solvent was removed under vacuum with a rotavapor. The remaining water fraction was lyophilized for 48 h. The extract had a polyphenol content (Folin) of 31.75%.
Methods The effects of the compositions on the skin were evaluated by the following methods:
1. Hydration: corneometry (dielectric value measured with 2 metal electrodes)

Moisturization was evaluated by corneometry measurement with a Corneometer CM 835® from Courage+Khazaka electronic GmbH (Köln, Germany). Since 1980 the Corneometer® has provided a well established method to reproducibly and accurately determine the hydration level of the skin surface. The measuring principle of the Corneometer® CM 825 is based on capacitance measurement of a dielectric medium. Any change in the dielectric constant due to skin surface hydration variation alters the capacitance of a precision measuring capacitor.
2. Skin barrier function: TEWL (transepidermal water loss)

The measurement of transepidermal water loss (TEWL) is important for evaluating the efficiency of the skin water barrier. This measurement is performed using a tewameter TM 300® from Courage+Khazaka electronic GmbH. The measurement of the water evaporation is based on the diffusion principle in an open chamber. Separate measurements were carried out on the skin of the face and the skin of the body.
3. Skin restructuring activity: microscopic evaluation on reprint made in cyanoacrylate Specific analyses of the micro-relief on skin surface wrinkles are performed: characteristic parameters such as primary lines, secondary lines, polygons, etc are studied and allow determination of the skin structure.
Results The following results were obtained in the experiments.

|  | Hydration (% increase) | Skin Barrier Function - Face TEWL (g/hm²) | Skin Barrier Function - Body TEWL (g/hm²) | Restructuring activity % change |
|---|---|---|---|---|
| Control | 6 | −5 | −4 | 0 |
| Invention | 20 | −18 | −19 | 4 |
| Comparative Example | 6 | −11 | −12 | 6 |

The results show that the composition of the invention, i.e., an extract from non-defatted cocoa beans, increases hydration and improves skin barrier function, as well as showing an effect on restructuring. The composition of the invention was superior to a corresponding extract from defatted cocoa beans.

The invention claimed is:

1. Method for improving skin health in a subject in need thereof, comprising orally administering an effective amount of a cocoa extract, to the subject in need thereof, wherein the cocoa extract is obtained by the extraction of non-defatted cocoa beans which have not been fermented or have been allowed to ferment for no more than three days, having a polyphenol content of more than 25% by weight, wherein the extract comprises from 0.1 to 10% by weight of cocoa fats.

2. Method for improving skin health in a subject, comprising orally administering an effective amount of a cocoa extract, to the subject in need thereof, wherein the cocoa extract is obtained by the extraction of non-defatted cocoa beans which have not been fermented or have been allowed to ferment for no more than three days, having a polyphenol content of more than 25% by weight, wherein the improvement in skin health comprises one or more of: increased firmness, increased elasticity, increased tonicity, reduced fine lines, increased hydration, decreased skin roughness, decreased scaling, improved skin structure (including skin barrier), or depigmenting (or lightening) age spots and the extract is in the form of a tablet, pill, capsule, caplet, multiparticulate, powder, elixir, syrup, suspension, or solution.

3. Method for improving skin health in a subject, comprising orally administering an effective amount of a cocoa extract, to the subject in need thereof, wherein the cocoa extract is obtained by the extraction of non-defatted cocoa beans which have not been fermented or have been allowed to ferment for no more than three days, having a polyphenol content of more than 25% by weight, wherein the improvement in skin health comprises one or more of: increased firmness, increased elasticity, increased tonicity, reduced wrinkles (including wrinkle width and/or volume), reduced fine lines, increased hydration, decreased skin roughness, decreased scaling, improved skin structure (including skin barrier), or depigmenting (or lightening) age spots and the extract is in the form of a foodstuff or confectionery product.

4. The method of claim 1, wherein the extract has a polyphenol content of at least 30% by weight.

5. The method of claim 1, wherein the extract has a polyphenol content of from 30 to 70% by weight.

6. The method of claim 1, wherein the extract has a theobromine content of at least 5% by weight.

7. The method of claim 1, wherein the extract has a theobromine content of less than 5% by weight.

8. The method of claim 1, wherein the extract is obtained by solvent extraction of the cocoa beans.

9. The method of claim 8, wherein the solvent is selected from C1 to C6 alcohols or ketones, and mixtures thereof, optionally in admixture with water.

10. The method of claim 9, wherein the solvent is selected from ethanol, acetone, 2-butanol, 2-propanol and mixtures thereof, optionally in admixture with water.

11. The method of claim 1, wherein the extract comprises less than 2% by weight phenylethylamine.

12. The method of claim 1, wherein the extract comprises from 0.2 to 5% by weight of cocoa fats.

13. The method of claim 1, wherein the cocoa fats are non-triglyceride lipids.

14. The method of claim 1, wherein the extract comprises:
 (i) from 35 to 70% by weight cocoa polyphenols;
 (ii) from 1 to 10% by weight xanthines;
 (iii) less than 2% by weight phenylethylamine; and
 (iv) from 0.1 to 10% by weight of cocoa fats.

15. The method of claim 1, wherein the extract comprises from 15 to 40% by weight protein.

16. The method of claim 1, wherein the extract comprises from 2 to 12% by weight sugars.

17. The method of claim 1, wherein the extract is provided as part of a food or confectionery product.

18. The method of claim 1, wherein the extract is provided as a cosmetic composition or supplement.

* * * * *